(12) United States Patent
Scott et al.

(10) Patent No.: US 11,090,373 B2
(45) Date of Patent: Aug. 17, 2021

(54) ANTIGEN-SPECIFIC T CELLS FOR INDUCING IMMUNE TOLERANCE

(71) Applicant: The Henry M. Jackson Foundation for the Advancement of Military Medicine, Inc., Bethesda, MD (US)

(72) Inventors: David W. Scott, Bethesda, MD (US); Yongchan Kim, Rockville, MD (US); Aihong Zhang, Ellicott City, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 15/780,584

(22) PCT Filed: Oct. 6, 2016

(86) PCT No.: PCT/US2016/055656
§ 371 (c)(1),
(2) Date: May 31, 2018

(87) PCT Pub. No.: WO2017/095525
PCT Pub. Date: Jun. 8, 2017

(65) Prior Publication Data
US 2018/0369350 A1 Dec. 27, 2018

Related U.S. Application Data

(60) Provisional application No. 62/263,108, filed on Dec. 4, 2015, provisional application No. 62/359,886, filed on Jul. 8, 2016, provisional application No. 62/393,245, filed on Sep. 12, 2016.

(51) Int. Cl.
| | | |
|---|---|---|
| A61K 35/17 | (2015.01) | |
| C12N 5/07 | (2010.01) | |
| C07K 14/755 | (2006.01) | |
| C12N 5/0783 | (2010.01) | |
| A61P 37/06 | (2006.01) | |
| A61K 39/00 | (2006.01) | |
| A61P 21/04 | (2006.01) | |
| A61P 3/10 | (2006.01) | |

(52) U.S. Cl.
CPC .......... *A61K 39/0008* (2013.01); *A61K 35/17* (2013.01); *A61P 3/10* (2018.01); *A61P 21/04* (2018.01); *A61P 37/06* (2018.01); *C12N 5/0637* (2013.01); *C12N 5/0638* (2013.01); *A61K 2039/5156* (2013.01); *A61K 2039/5158* (2013.01); *C12N 2502/1107* (2013.01); *C12N 2510/00* (2013.01)

(58) Field of Classification Search
CPC ................ A61K 39/0008; A61K 35/17; A61K 2039/5156; A61K 2039/5158; A61K 2039/572; A61K 2039/577; A61K 2038/5156; A61K 2039/57; C12N 5/0638; C12N 5/0637; C12N 2510/00; C12N 5/0639; C12N 2502/11; C12N 2502/1114; C07K 14/70521; C07K 14/7651

See application file for complete search history.

(56) References Cited

U.S. PATENT DOCUMENTS

| | | | | |
|---|---|---|---|---|
| 7,214,785 | B2* | 5/2007 | Nakashima | C07K 7/06 424/134.1 |
| 2013/0287748 | A1* | 10/2013 | June | A61K 35/17 424/93.21 |
| 2015/0017141 | A1 | 1/2015 | June et al. | |
| 2016/0264662 | A1* | 9/2016 | Dimitrov | A61K 47/6803 |

FOREIGN PATENT DOCUMENTS

WO    WO-2012079000 A1 *    6/2012    ....... C07K 14/70596

OTHER PUBLICATIONS

Lloyd et al., Protein Engineering, Design & Selection 22:159-168 (Year: 2009).*
Edwards et al., J Mol Biol 334(1): 103-118 (Year: 2003).*
Fransson et al., J Neuroinflammation 9:112-12 (Year: 2012).*
Adair et al., Frontiers in Immunology 8: 1-10 (Year: 2017).*
Fransson et al., "CAR/FoxP3-engineered T regulatory cells target the CNS and suppress EAE upon intranasal delivery," Journal of Neuroinflammation, vol. 9, No. 1, pp. 1-12, (Jan. 2012) XP055108972.
Maus et al., "Antibody-modified T cells: CARs take the front seat for hematologic malignancies," Blood, vol. 123, No. 17, pp. 2625-2635, (Apr. 2014), XP055278960.
Naumann et al., "Generation and Characterization of FVIII-Specific CAR-Transduced Regulatory T Cells," Blood, vol. 124, No. 21, p. 236 (Abstract only) (Dec. 2014) XP055590739.
Parvathaneni et al., "BAR-CD8 T-Cell Mediated Targeted Killing of Inhibitor Producing FVIII-Specific B Cells," Blood, vol. 126, No. 23, p. 294 (Abstract only) (Dec. 2015) XP055590702.
Thorburn et al., "Harnessing Regulatory T cells to Suppress Asthma," American Journal of Respiratory Cell and Molecular Biology, vol. 43, No. 5, pp. 511-519 (Nov. 2010) XP055032545.
Wroblewska, "Dangerous liaisons: how the immune system deals with factor VIII," Journal of Thrombosis and Haemostasis, vol. 11, No. 1, pp. 47-55, (Jan. 2013) XP055294470.
Zhang et al., "Subsets of regulatory T cells and their roles in allergy," Journal of Translational Medicine, Biomed Central, vol. 12, No. 1, p. 125 (May 2014) XP021186612.
Extended European Search Report dated Jun. 6, 2019 in European Application No. 16871218.0.
De Wit et al., "Antigen-Specific B Cells Reactivate an Effective Cytotoxic T Cell Response against Phagocytosed *Salmonella* through Cross-Presentation", PloS One, (Sep. 2010), vol. 5, Issue 9, Article No. e13016.

(Continued)

*Primary Examiner* — Phuong Huynh
(74) *Attorney, Agent, or Firm* — Potomac Law Group, PLLC

(57) ABSTRACT

Described herein are agents and methods for targeting antigen-specific B cells using engineered T cells, such as regulatory T cells or cytotoxic T cells, or bi-specific antibodies. The agents and methods can be used to reduce undesirable immune responses.

16 Claims, 20 Drawing Sheets

(56) References Cited

OTHER PUBLICATIONS

Figure 3:
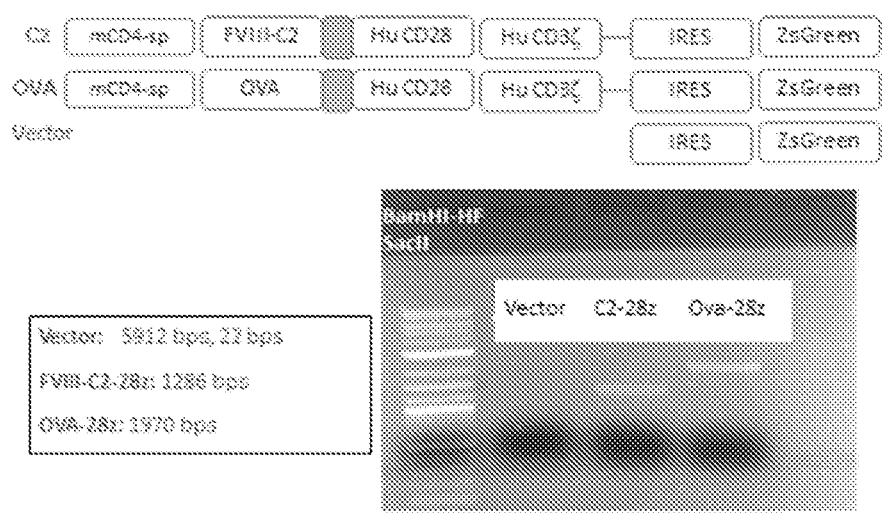

Ellebrechtl et al., "Desmoglein 3 chimeric autoantibody receptor T cells a novel strategy for immunotherapy of pemphigus vulgaris (THER2P.958)", The Journal of Immunology (May 2015) vol. 194 (1 Supplement) 67.9 (Abstract).

Kim et al., "Engineered antigen-specific human regulatory T cells: immunosuppression of FVIII-specific T- and B-cell responses", Blood (Feb. 2015), vol. 125, No. 7, pp. 1107-1115 (available on-line Dec. 2014).

Kim et al., "Oligodeoxynucleotides stabilize Helios-expressing Foxp3+ human T regulatory cells during in vitro expansion", Blood (2012), vol. 119, pp. 2810-2818.

Lacroix-Desmazes et al., "Dynamics of factor VIII interactions determine its immunologic fate in hemophilia A", Blood (Jul. 2008), vol. 112, No. 2, pp. 240-249.

Lee et al., "T cells expressing CD19 chimeric antigen receptors for acute lymphoblastic leukaemia in children and young adults: a phase 1 dose-escalation trial", The Lancet (Feb. 2015) vol. 385, pp. 517-528.

Miao et al., "CD4+ FOXP3+ regulatory T cells confer long-term regulation of factor VIII-specific immune responses in plasmid-mediated gene therapy-treated hemophilia mice", Blood (Nov. 2009) vol. 114, No. 19, pp. 4034-4444.

Pincus et al., "Characterization of T Cells Bearing HLA-DR Antigens in Rheumatoid Arthritis", Arthritis and Rheumatism (Jan. 1985) vol. 28, No. 1, pp. 517-528.

Skupsky et al., "Role of Adaptive Regulatory T Cells in the Induction of Tolerance to FVIII", Blood (2008) vol. 112, No. 11, p. 1027 (Abstract).

Zhang "Targeting antigen-specific B cells using BAR-transduced cytotoxic and regulatory T cells", The American Association of Immunologists, Inc. (May 2016) presentation.

Zhang et al., "Targeting antigen-specific B cells using BAR-transduced cytotoxic and regulatory T cells", The Journal of Immunology (May 2016), vol. 196, No. 1, Supplement 70.7 (available on-line Apr. 2016).

Dang et al., "1F7 (CD26): a marker of thymic maturation involved in the differential regulation of the CD3 and CD2 pathways of human thymocytes activation," The Journal of Immunology, 1991, vol. 147(9), pp. 2825-2832, The American Associate of Immunologists, Minneapolis, Minnesota.

Daraiavach et al., "Human Ig superfamily CTLA-4 gene: chromosomal localization and identity of protein sequence between murine and human CTLA-4 cytoplasmic domains*," European Journal of Immunology, 1988, vol. 18(12), pp. 1901-1905, John Wiley & Sons, Inc., New Jersey.

Graw et al., "Haemophilia A: From Mutations Analysis to New Therapies," Nature Review Genetics, 2005, vol. 6, pp. 488-501, Nature Publishing Group, Berlin, Germany.

Harper et al., "CTLA-4 and CD28 Activated Lymphocyte Molecules Are Closely Related in Both Mouse and Human as to Sequence, Message Expression, Gene Structure, and Chromosomal Location," The Journal of Immunology, 1991, vol. 147(3), pp. 1037-1044, The American Associate of Immunologists, Minneapolis, Minnesota.

Hutloff et al., "ICOS is an inducible T-cell co-stimulator structurally and functionally related to CD28," Nature, 1999, vol. 397, pp. 263-266, Macmillan Magazines Ltd, London, United Kingdom.

Kwon et al., "cDNA sequences of two inducible T-cell genes," Proc. Natl. Acad. Sci., 1989, vol. 86, pp. 1963-1967.

Lafage-Pochitaloff et al., "Human CD28 and CTLA-4 IG superfamily genes are located on chromosome 2 at bands q33-q34," Immunogenetics, 1990, vol. 31, pp. 198-201, Springer-Verlag, Berlin, Germany.

NCBI, "*Homo sapiens* CD247 molecule (CD247), transcript variant 1, mRNA," GenBank accession No. NM_198053.3 (May 13, 2020).

NCBI, "*Homo sapiens* CD28 molecule (CD28), transcript variant 1, mRNA," GenBank accession No. NM_006139.4 (Jul. 4, 2020).

NCBI, "*Homo sapiens* coagulation factor VIII(F8), transcript variant 1, mRNA," GenBank accession No. NM_000132.4 (May 13, 2020).

NCBI, "*Homo sapiens* cytotoxic T-lymphocyte associated protein 4 (CTLA4), transcript variant 1, mRNA," GenBank accession No. NM_005214.5 (Jul. 4, 2020).

NCBI, "*Homo sapiens* inducible T cell costimulator (ICOS), mRNA," GenBank accession No. NM_012092.4 (May 12, 2020).

NCBI, "*Homo sapiens* TNF receptor superfamily member 9 (TNFRSF9), mRNA," GenBank accession No. NM_001561.6 (May 12, 2020).

Osman et al., "Evidence from an association between the T cell receptor/CD3 antigen complex and the CD5 antigen in human T lymphocytes," Eur. J. Immunol., 1992, vol. 22, pp. 2995-3000, Wiley-VCH, Weinheim, Germany.

Truett et al., "Characterization of the Polypeptide Composition of Human Factor VIII:C and the Nucleotide Sequence and Expression of the Human Kidney cDNA," DNA, 1985, vol. 4(5), pp. 33-349, Mary Ann Liebert, Inc., New Rochelle, New York.

Weissman et al., "Molecular cloning and chromosomal localization of the human T-cell receptor chain: Distinction from the molecular CD3 complex," Proc. Natl. Acad. Sci., 1988, vol. 85, pp. 9709-9713.

Zhou et al., "Characterization of human homologue of 4-1BB and its ligand," Immunology Letters, 1995, vol. 45, pp. 67-73, Elsevier Science B.V., Amsterdam, Netherlands.

Zucker et al., "Factor VIII-related antigen in human blood platelets: localization and release by thrombin and collagen," J. Lab. Clin. Med., 1979, vol. 94(5). pp. 675-682.

\* cited by examiner

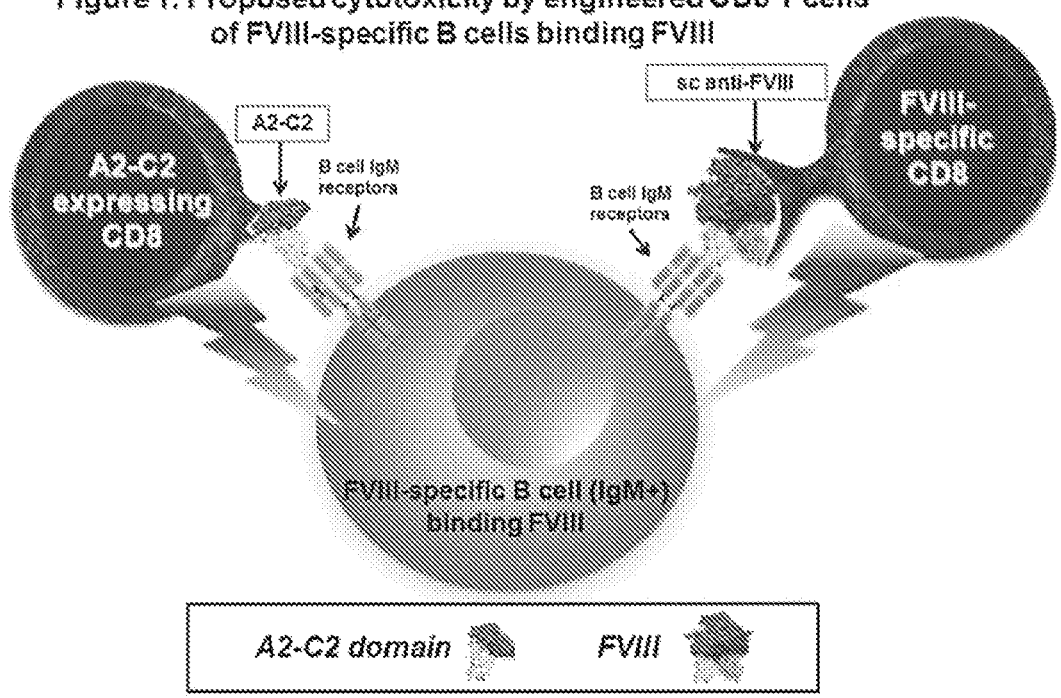

Figure 2. Potential CD8:FVIII targeting bi-specific antibodies.

*Generation and expression of BAR on human CD4+ T cells*

*Generation and expression of BAR on human CD4+ T cells*

*Generation and expression of BAR on human CD4+ T cells*

US 11,090,373 B2

ANTIGEN-SPECIFIC T CELLS FOR INDUCING IMMUNE TOLERANCE

CROSS-REFERENCE TO RELATED APPLICATIONS

This application is the U.S. National Stage of International Application PCT/US2016/055656, filed Oct. 6, 2016, which claims the benefit under 35 U.S.C. § 119(e) to U.S. Provisional Application No. 62/263,108, filed Dec. 4, 2015, U.S. Provisional Application No. 62/359,886, filed Jul. 8, 2016, and U.S. Provisional Application No. 62/393,245, filed Sep. 12, 2016. The contents of these applications are incorporated by reference herein in their entireties.

GOVERNMENT LICENSE RIGHTS

This invention was made with government support under R21 HL127495, RO1 HL126727 and RO1 HL061833 awarded by the National Institutes of Health. The government has certain rights in the invention.

FIELD

Described herein are agents and methods for targeting antigen-specific B cells using engineered T cells, such as cytotoxic T cells or regulatory T cells, or bispecific antibodies. The agents and methods can be used to induce immune tolerance, e.g., to reduce undesirable immune responses.

BACKGROUND

Many therapies can induce undesired immune responses, such as antibody responses to therapeutic proteins or allergens or toxins used as immunotoxins. Undesired immune responses also may arise in the context of transplant rejection, allergies, allergic responses, and asthma. Thus, it may be desirable to suppress immune responses to therapeutic agents, allograft transplants, and allergens.

Methods for immunosuppression have been disclosed that involve expanding non-specific regulatory T cells. However, non-specific regulatory T cells can suppress desired immune responses, such as responses to pathogenic infections and cancer. Thus, there remains a need for a more targeted approach to immunosuppression.

One example of a potentially immunogenic therapeutic agent is clotting Factor VIII (FVIII), used to treat hemophilia. Hemophilia is the second most common congenital bleeding disorder and is characterized by frequent bleeds at joint levels resulting in cartilage fibrosis, loss of joint space, and debilitation. Hemophilia affects the knees, ankles, hips, shoulders, elbows and bleeding into closed spaces can be fatal. Hemophilia A is caused by a genetic deficiency in clotting factor VIII, an essential blood-clotting protein. Depending on the mutation, hemophilia A patients lack all or part of the FVIII protein. Currently, treatment methods for hemophilia consist of infusions of either recombinant or plasma-derived clotting factor concentrates, usually administered in response to bleeds. However, greater than 20% of hemophilia A patients exhibit undesired immune responses against these protein therapies, and make antibodies against therapeutic FVIII proteins that undermine the treatment and inhibit clotting. Conventional FVIII therapies also require frequent injection/infusion over the patient's lifetime, and are associated with very high costs.

Thus, there exists a need for effective approaches to reducing undesirable immune responses, such as undesirable immune responses to therapeutic agents, allograft transplants, and allergens.

SUMMARY

Described herein are agents and methods for targeting antigen-specific B cells using engineered T cells, such as regulatory T cells of cytotoxic T cells, or bispecific antibodies. The agents and methods can be used to reduce undesirable immune responses, as discussed in more detail below.

In accordance with some embodiments, there are provided methods of targeting antigen-specific B cells, comprising exposing B cells specific to a target antigen to regulatory T cells that express on their cell surface the target antigen or a domain thereof recognized by the antigen-specific B cells. Also provided are methods of targeting antigen-specific B cells, comprising exposing B cells specific to a target antigen to (i) regulatory T cells that express on their cell surface a single chain antibody specific for the target antigen, and (ii) the target antigen. In some embodiments, the single chain antibody is bound to the target antigen or domain thereof recognized by the antigen specific B cells before exposure to the antigen specific B cells. Also provided are methods of targeting antigen-specific B cells, comprising exposing B cells specific to a target antigen to regulatory T cells bound by a bi-specific antibody comprising a T cell-binding end and a B cell-targeting end, wherein the B cell-targeting end comprises a domain of the target antigen recognized by the antigen-specific B cells. In any of these embodiments, the regulatory T cells may be selected from $CD4^+CD25^{hi}CD127^{lo}Foxp3^+$ regulatory T cells, $CD4^+CD25$ $CD127^{lo}Foxp3^+Helios^+$ regulatory T cells, $CD4^+CD25^{hi}Foxp3^+$ regulatory T cells, and $CD4^+CD25^{hi}Foxp3^+Helios^+$ regulatory T cells.

In accordance with some embodiments, there are provided methods of targeting antigen-specific B cells, comprising exposing B cells specific to a target antigen to cytotoxic T cells that express on their cell surface the target antigen or a domain thereof recognized by the antigen-specific B cells. Also provided are methods of targeting antigen-specific B cells, comprising exposing B cells specific to a target antigen to (i) cytotoxic T cells that express on their cell surface a single chain antibody specific for the target antigen and (ii) the target antigen. In some embodiments, the single chain antibody is bound to the target antigen or domain thereof recognized by the antigen specific B cells before exposure to the antigen specific B cells. Also provided are methods of targeting antigen-specific B cells, comprising exposing B cells specific to a target antigen to cytotoxic T cells bound by a bi-specific antibody comprising a T cell-binding end and a B cell-targeting end, wherein the B cell-targeting end comprises a domain of the target antigen recognized by the antigen-specific B cells. In accordance with any of these methods, the cytotoxic T cell may be selected from CD8+ T cells and natural killer (NK) T cells.

In accordance with any of the methods, the cytotoxic T cells or regulatory T cells may be transduced with a B-cell-targeting antibody receptor (BAR) construct comprising (i) an extracellular domain comprising the target antigen or domain thereof and (ii) an intracellular signaling domain. In accordance with any of these methods, the intracellular signaling domain may comprise one or more signaling domains, such as one or more signaling domains from CD28-CD3ζ, 4-1BB, ICOS, and CTLA-4.

In accordance with any of these methods, the target antigen may be a therapeutic agent, such as a therapeutic protein or an allergen or toxin used as an immunotoxin. In some embodiments, the target antigen is associated with an autoimmune disorder, such as multiple sclerosis, diabetes, uveitis, thyroiditis, myasthenia gravis, antiphospholipid syndrome (APS), or an undesired immune response to a therapeutic agent, such as a biotherapeutic agent used to treat a genetic disease, such as hemophelia or Pompe's, or an allergen or antigen used as an immunotoxin, or may be associated with an allergy, allergic response or asthma, or may be an antigen of an allograft transplant. In some embodiments, the target antigen is a therapeutic protein selected from human clotting factor VIII, the C2 domain of human clotting factor VIII, the A-2 domain of human clotting factor VIII, and the A2-C2 domain of human clotting factor VIII, human clotting factor IX, myelin basic protein (MBP) or other antigens associated with multiple sclerosis, an antigen associated with diabetes, an antigen associated with uveitis, an antigen associated with thyroiditis, an antigen associated with myasthenia gravis, an antigen associated with antiphospholipid syndrome (APS), an antigen of an allograft transplant, such as a cell, tissue, or organ of an allograft transplant, or an antigen associated with an allergy or allergic response, or asthma.

In accordance with any of these methods, the method may be effected in a patient suffering from or at risk of developing an undesirable immune response to the target antigen. In some embodiments, the patient is suffering from an autoimmune disorder, such as one or more selected from the multiple sclerosis, diabetes, and uveitis, and/or is receiving a biotherapeutic treatment for a genetic disease, such as Pompe's, hemophilia (including hemophilia A and hemophilia B), thyroiditis, or myasthenia gravis, and/or is receiving an allograft transplant. In specific embodiments, the patient is suffering from or at risk of developing an undesired immune response to Factor VIII therapy. In some embodiments, the method is effective to reduce or prevent the patient's immune response to the target antigen.

Also provided are regulatory T cells that express on their cell surface a target antigen or a domain thereof recognized by an antigen-specific B cell. In accordance with any of these embodiments, the regulatory T cell may be transduced with a B-cell-targeting antibody receptor (BAR) construct comprising (i) an extracellular domain comprising the target antigen or domain thereof and (ii) an intracellular signaling domain. In some embodiments, the intracellular signaling domain comprises one or more signaling domains, such as one or more signaling domains from CD28-CD3ζ, 4-1BB, ICOS, and CTLA-4. Also provided are regulatory T cells that expresses on their surface a single chain antibody specific for a target antigen. Also provided are regulatory T cells bound by a bi-specific antibody comprising a T cell-binding end and a B cell-targeting end, wherein the B cell-targeting end comprises a domain of a target antigen recognized by an antigen-specific B cell. In accordance with any of these embodiments, the regulatory T cells may be isolated using CD4, CD25, CD127 cell surface markers. In any of these embodiments, the regulatory T cells may be selected from CD4$^+$CD25$^{hi}$CD127$^{lo}$Foxp3$^+$ regulatory T cells, CD4$^+$CD25$^{hi}$CD127$^{lo}$Foxp3$^+$Helios$^+$ regulatory T cells, CD4$^+$CD25$^{hi}$Foxp3$^+$ regulatory T cells, and CD4$^+$CD25$^{hi}$Foxp3$^+$Helios$^+$ regulatory T cells.

Also provided are cytotoxic T cells that express on their cell surface a target antigen or a domain thereof recognized by an antigen-specific B cell. In accordance with any of these embodiments, the cytotoxic T cell may be transduced with a B-cell-targeting antibody receptor (BAR) construct comprising (i) an extracellular domain comprising the target antigen or domain thereof and (ii) an intracellular signaling domain. In some embodiments, the intracellular signaling domain comprises one or more signaling domains, such as one or more signaling domains from CD28-CD3ζ, 4-1BB, and ICOS. Also provided are cytotoxic T cells that expresses on their cell surface a single chain antibody specific for a target antigen. Also provided are cytotoxic T cells bound by a bi-specific antibody comprising a T cell-binding end and a B cell-targeting end, wherein the B cell-targeting end comprises a domain of a target antigen recognized by an antigen-specific B cell. In accordance with any of these embodiments, the cytotoxic T cell may be selected from CD8+ T cells and natural killer (NK) T cells.

In accordance with any of these embodiments, the target antigen may be any one or more as discussed above with regard to methods.

Also provided are regulatory T cells or cytotoxic T cells as described herein, for use in reducing undesired immune responses, inducing immune tolerance, treating autoimmune diseases or disorders, or enhancing a patient's response to a biotherapeutic treatment for a genetic disease.

Also provided are uses of regulatory T cells or cytotoxic T cells as described herein in the preparation of medicaments for reducing undesirable immune responses, inducing immune tolerance, treating autoimmune diseases or disorders, or enhancing a patient's response to a biotherapeutic treatment for a genetic disease.

BRIEF DESCRIPTION OF FIGURES

FIG. 1. Overview of methods of targeting antigen-specific B cells by engineered CD8+ T cells as described herein. On the left, a CD8+ T cell engineered to express a target antigen domain (such as FVIII C2 and A2) binds to B cell IgM receptors on the surface of an FVIII-specific B cell. On the right, a CD8+ T cell engineered to express a single chain antibody specific for a target antigen (such as FVIII) bind to the target antigen (such as FVIII) which in turn is bound to an FVIII-specific B cell. In both approaches, the T cells induce killing of the antigen-specific B cells.

FIG. 2. Schematic of bi-specific antibodies comprising a T cell-binding end and a B cell-targeting end, wherein the B cell-targeting end comprises a domain of a target antigen recognized by an antigen-specific B cell. The target antigen domain (such as FVIII domains) is cloned into one IgG arm, and the T cell-binding moiety (e.g., anti-CD8 or NK marker) is cloned into the other arm. When the targeted antigen-specific B cells bind the antigen epitope of the bispecific antibody, the antibody-bound T cells induce killing of the antigen-specific B cells.

FIG. 3. Schematic illustration of construct used to make a FVIII-C2 B cell antibody receptor (BAR) construct. The genes (from N to C terminus) are: mouse CD4 N-terminal signaling peptide, FVIII-C2, human CD28 transmembrane, intracellular, human CD3, an internal ribosomal entry site (IRES) and GFP sequence. The IRES allows the BAR construct and GFP to be expressed as a single mRNA molecule, so that measurement of GFP correlates to BAR construct expression. A control constructing having the gene encoding OVA in place of the FVIII-C2 gene also is depicted (OVA-BAR construct).

FIG. 4. Expression of BAR in CD8 T cells. Isolated CD8+ T cells were activated and transduced with replication deficient BAR retrovirus using retronectin. 24 hrs post transduction, GFP expression can be visualized in both FVIII-C2 and OVA BAR transduced T cells.

Figure 5:
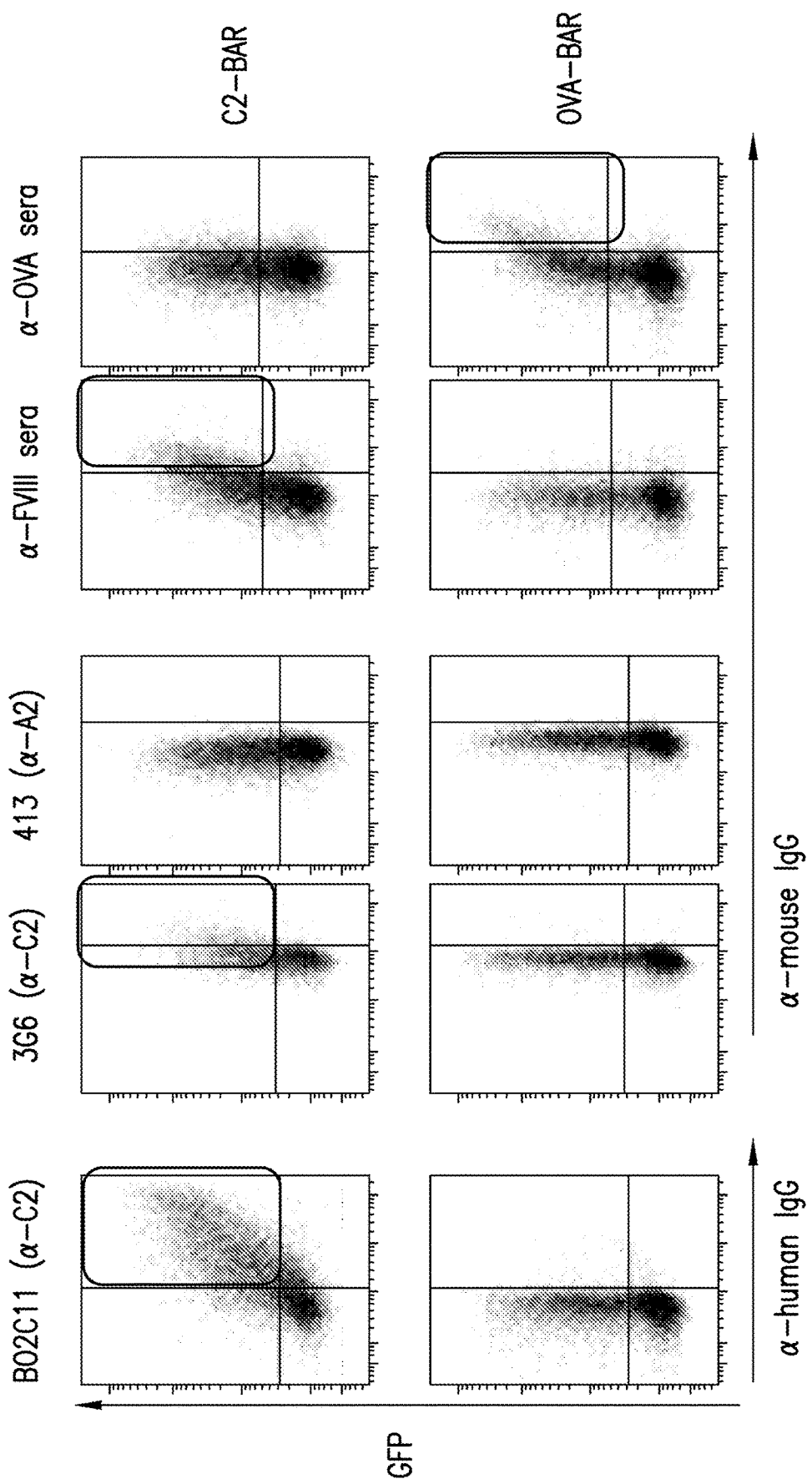

FIG. 5. Expression of BAR on T cell surface. The surface expression of the FVIII-C2 domain and OVA on the T cells is measured by flow cytometry using known antibodies against FVIII-C2 and OVA. FVIII-A2 antibody and anti-OVA were used as control.

Figure 6:
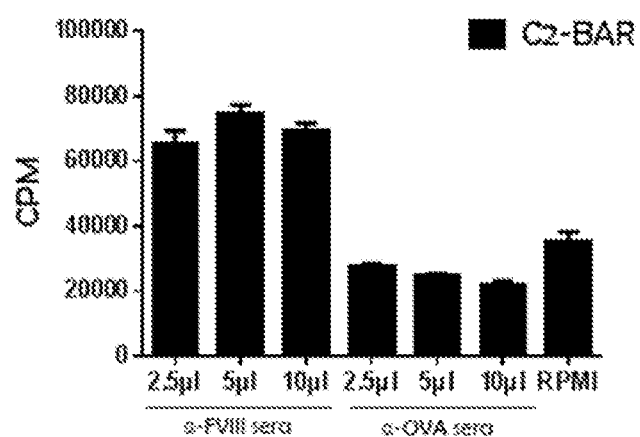

FIG. 6. Proliferation of BAR Transduced T cells. To observe the proliferation competency of the BAR expressing T cells, T cells were transduced and rested for 10 days, irradiated-PBMC pulsed with anti-FVIII sera were added at 2:1 to BAR expressing T cells. Cells were grown for 48 hrs and radioactive titrated thymidine uptake assay was performed for 24 hrs. The thymidine uptake by the proliferating T cells was measured. The figures show an increase in proliferation of C2-BAR T cells proliferation when anti-FVIII sera was used compared to the controls.

Figure 7:
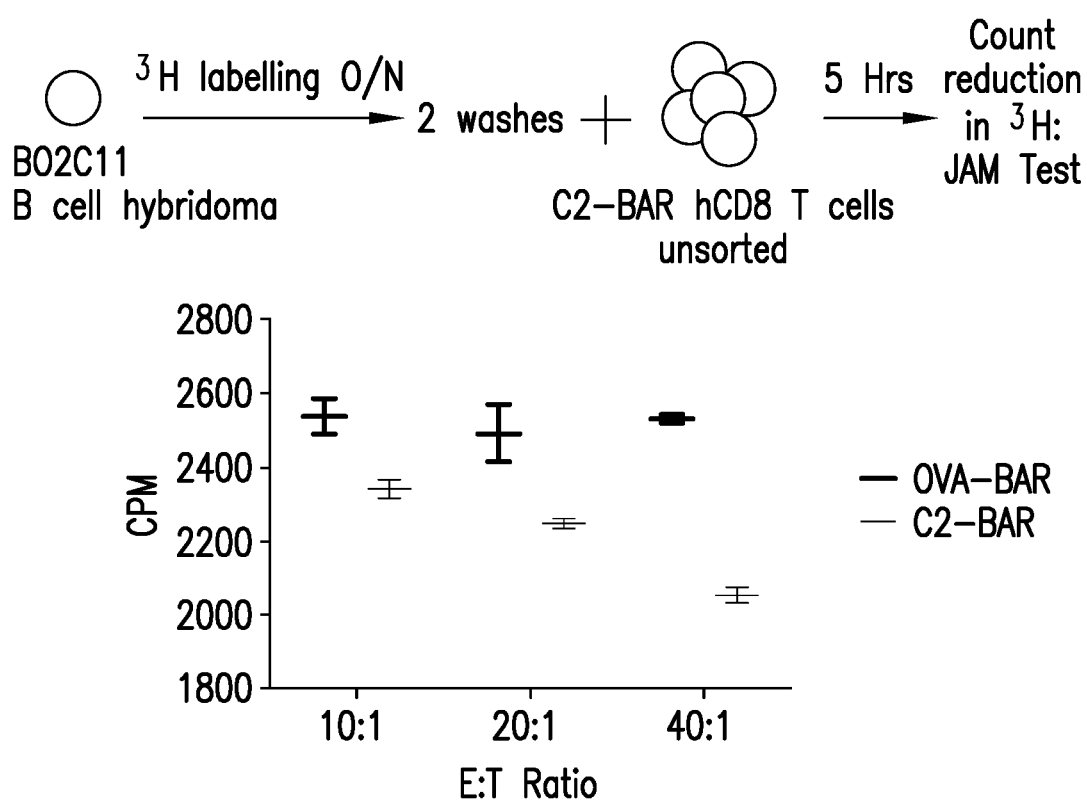

FIG. 7. FVIII-C2 BAR transduced CD8+ T cells are able to kill α-FVIII hybridoma, as shown by JAM test. 2C11 (anti-C2) B cell hybridoma cells were radiolabeled with titrated thymidine for 24 hrs and C2-BAR transduced CD8 T cells were added at various ratios and incubated for 5 hrs. At the end of the test, radioactivity was measured. The data shows a decrease in radiolabeled cells compare to that of ova controls, which corresponds to reduced viability of B cell hybridoma cells.

Figure 8:
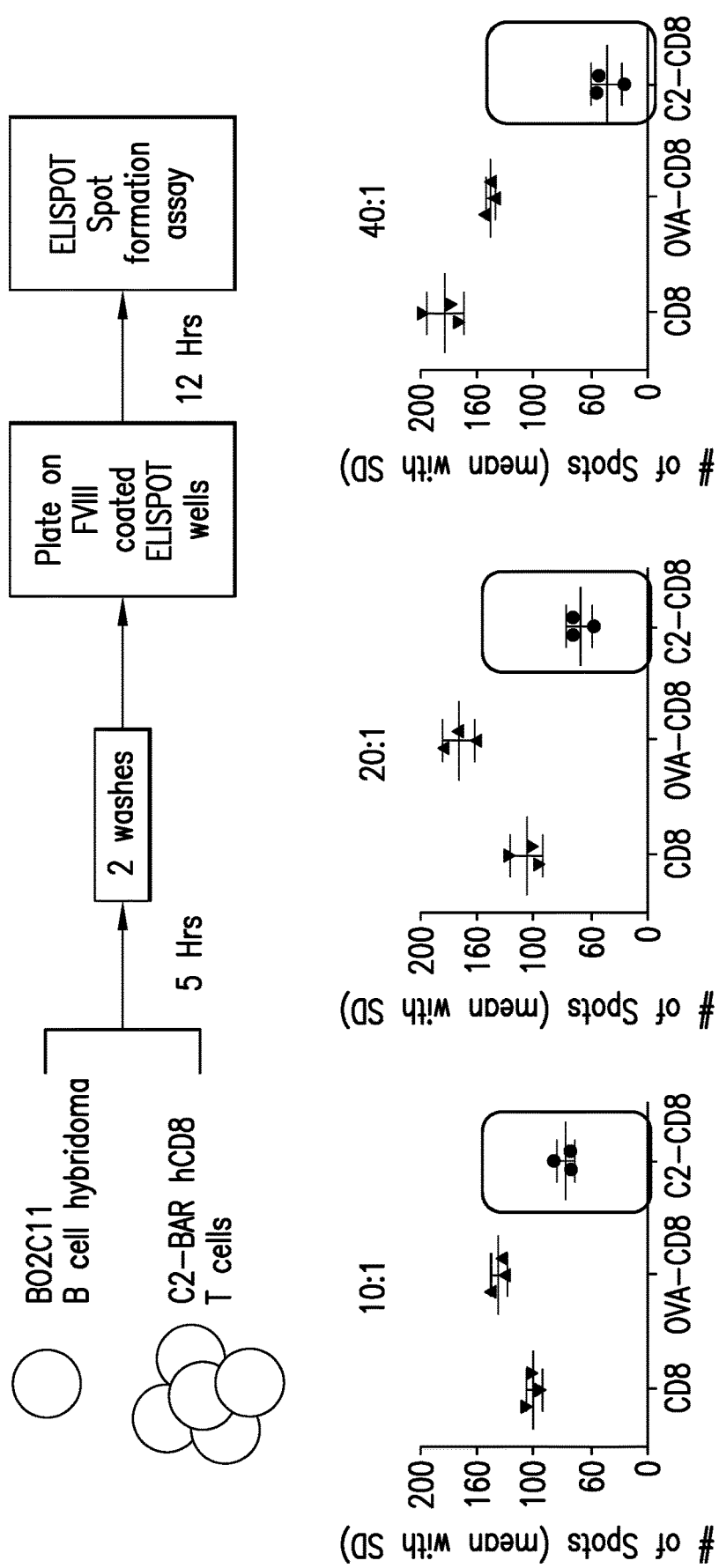

FIG. 8. FVIII-C2 BAR transduced CD8 T cells kill α-FVIII hybridoma shown by ELISPOT assay. 2C11 (anti-C2) B cell hybridoma cells were incubated with C2-BAR CD8 T cells at various ratios for 5 hrs and are then grown for 12 hrs on a FVIII coated plate. Number of spots formed at the end of the assay was quantified, a decrease in number of spots formed per well (correlates to number of viable antibody secreting B cells) in C2-BAR transduced CD8 T cells was detected compared to control.

Figure 9:
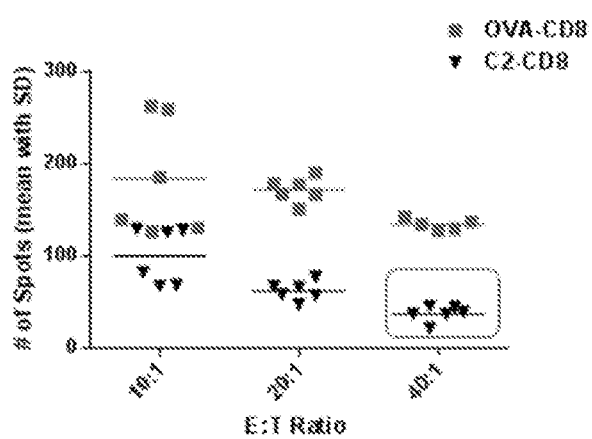

FIG. 9. Cumulative results of 3 individual ELISPOT performed under the same conditions.

Figure 10:
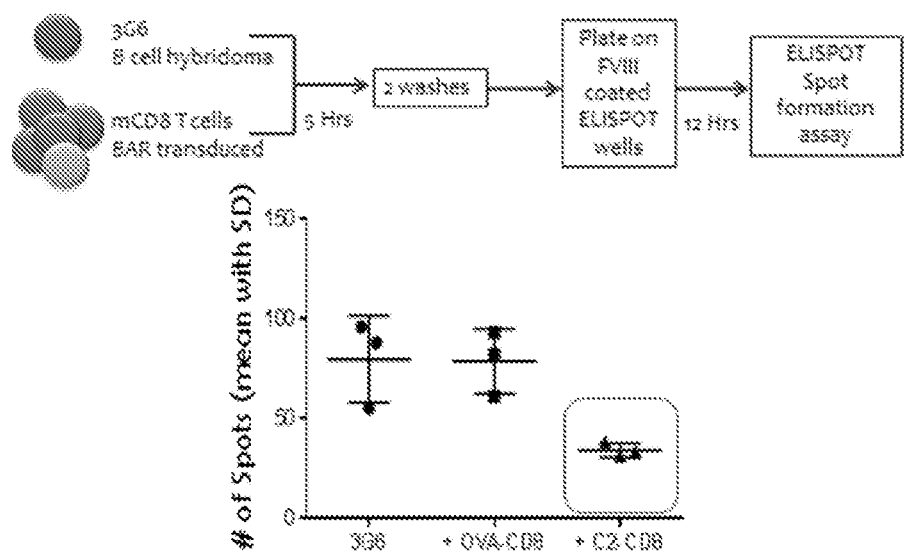

FIG. 10. FVIII-C2 BAR transduced CD8 T cells kill α-FVIII hybridoma, as shown by ELISPOT assay. 3G6 B cell hybridoma cells were incubated with C2-BAR transduced CD8 T cells at various ratios for 5 hrs and are then grown for 12 hrs on a FVIII coated plate. Number of spots formed at the end of the assay was quantified, the authors observed a decrease in number of spots formed per well (correlates to number of viable antibody secreting B cells) in C2-BAR transduced CD8 T cells compared to control.

Figure 11:
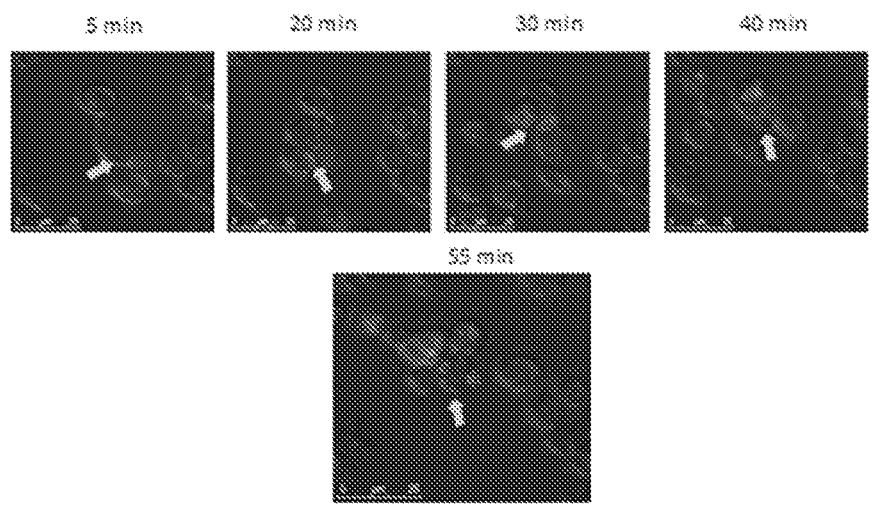

FIG. 11. Image of A2-BAR mediated cytolysis of α-FVIII hybridoma. A2-BAR transduced CD8 T cells are incubated with α-FVIII hybridoma. Images was taken at 5, 20, 30, 40 and 55 minutes after the incubation, cytolysis of the hybridoma was observed.

Figure 12:
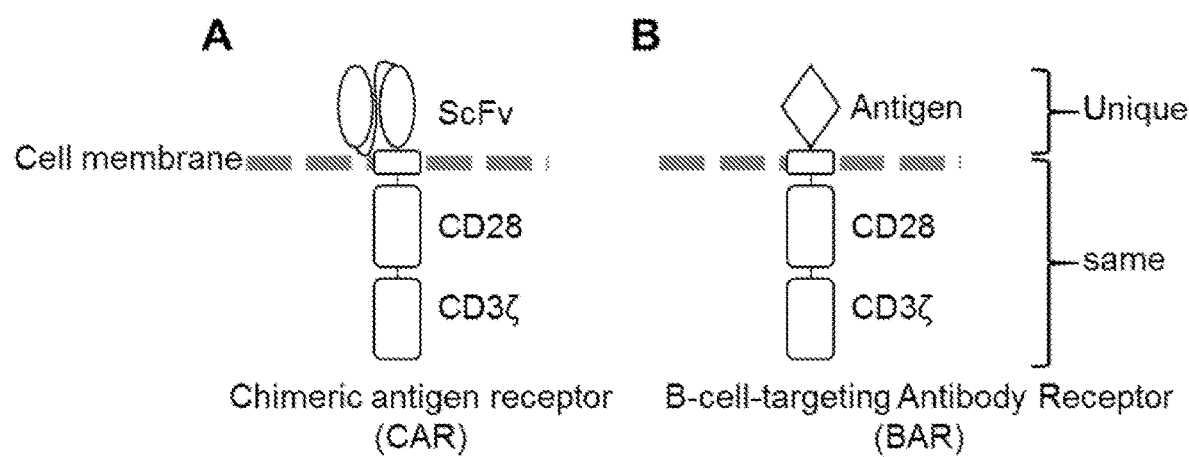

FIG. 12. Schematic diagram of chimeric antigen receptor (CAR) and B-cell-targeting antibody receptor (BAR). FIG. 12A illustrates CAR, wherein the extracellular domain is a single chain variable fragment (ScFv) of an antibody that recognizes a target antigen. FIG. 12B illustrates BAR, wherein the extracellular domain is a target antigen or domain thereof recognized by a B cell or antibody. The transmembrane and intracellular signaling domains of the illustrated CAR and BAR constructs comprise CD28-CD3.

Figure 13A:
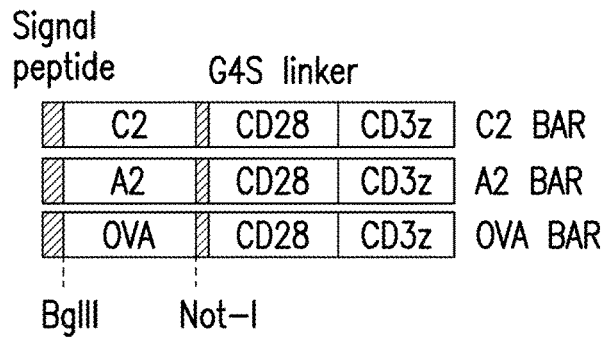
Figure 13B:
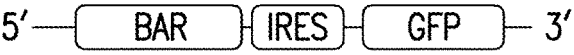
Figure 13C:
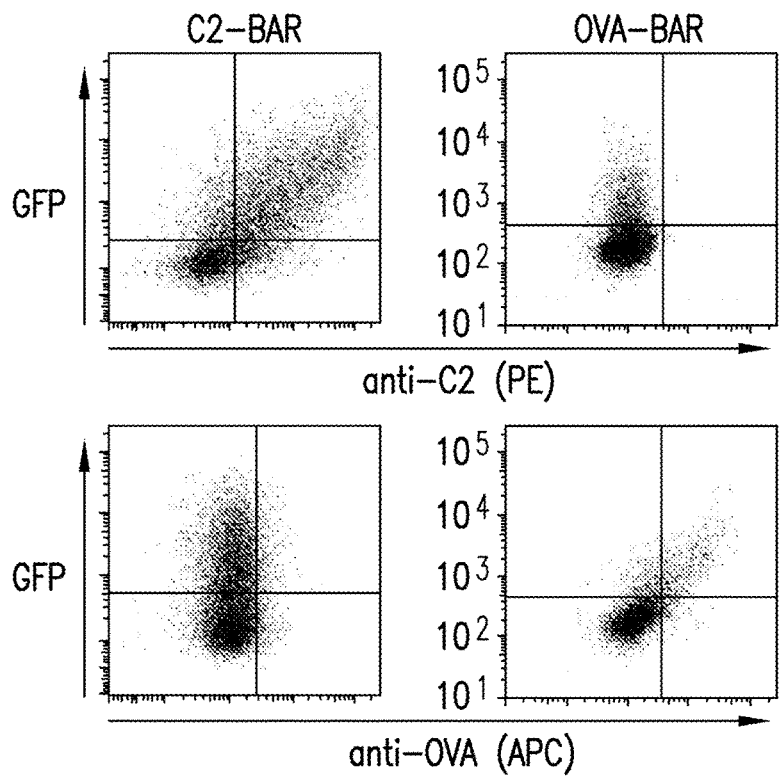

FIG. 13. Generation and expression of BAR on human CD4+ T cells. FIG. 13A is a schematic illustration of BAR constructs. The genes (from N to C terminus) are: signaling peptide, FVIII-C2 or FVIII-A2, human CD28-CD3ζ transmembrane/intracellular domains. A control construct having the gene encoding ovalbumin (OVA) also is depicted ("OVA BAR"). FIG. 13B illustrates an expression cassette of a retroviral vector encoding a BAR construct with a green fluorescent protein (GFP) reporter under the control of internal ribosomal entry site (IRES). The IRES allows the BAR construct and GFP to be expressed as a single mRNA molecule, so that measurement of GFP correlates to BAR construct expression. FIG. 13C shows the flow cytometry analysis of surface expression of C2 and OVA in transduced human CD4+ T cells by staining with monoclonal anti-C2 and polyclonal rabbit anti-OVA IgG, respectively, and demonstrates that BARs were successfully expressed on transduced cells.

Figure 14:
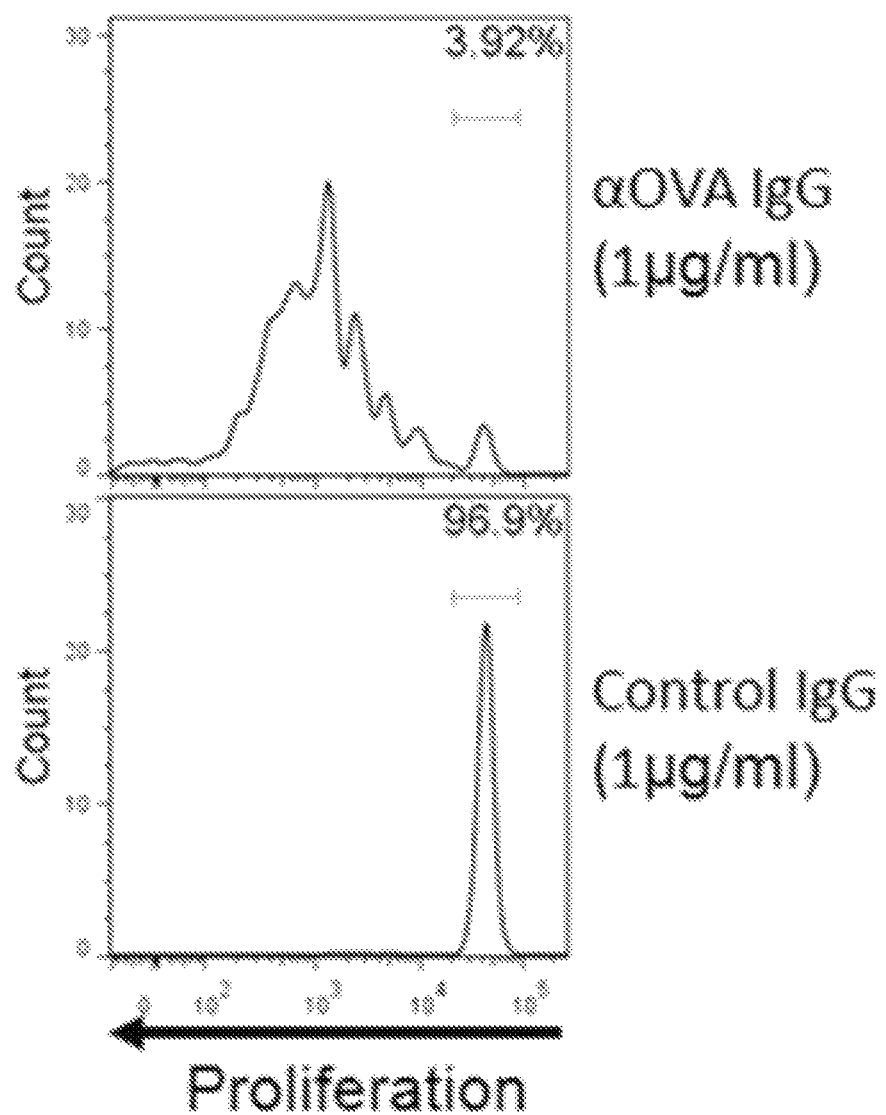

FIG. 14. Proliferation response of human CD4+ T cells expressing OVA-BAR to anti-OVA antibody. Human CD4+ T cells were FACS sorted from PBMC and transduced to express OVA-BAR using concentrated retroviral supernatant. Transduced cells were labeled with cell proliferation dye eFluor 450 and cultured with either anti-OVA IgG or control IgG for 3 days, in the presence of irradiated PBMC. Cell proliferation was analyzed by flow cytometry. The cells were gated on live GFP+ cells. This figure shows that OVA-BAR transduced T cells proliferated specific to anti-OVA IgG but not to control IgG, which confirms that the BAR expressed on the T cells is functional.

Figure 15:
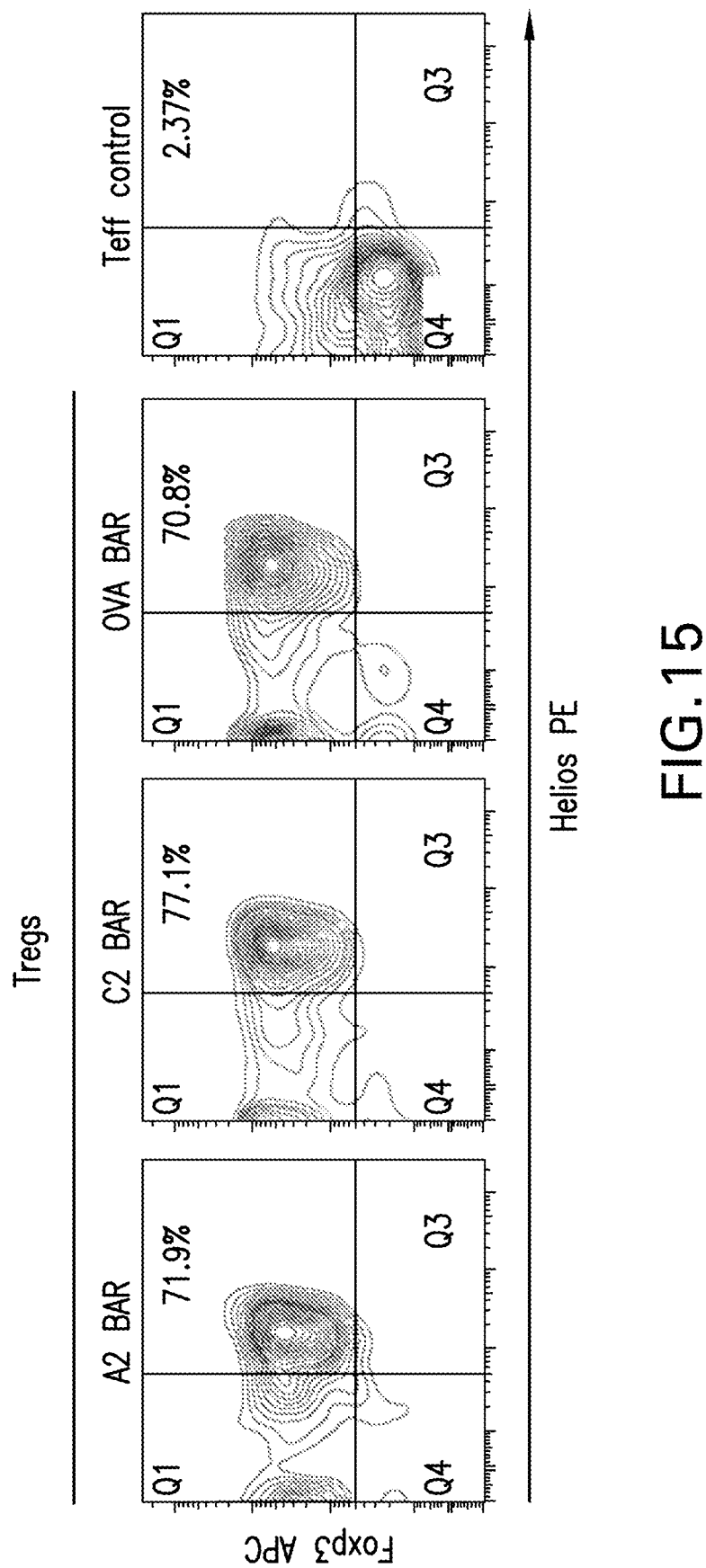

FIG. 15. FACS analysis of the quality of BAR-transduced regulatory T cells (Tregs) after about 3 weeks in vitro expansion. This figure shows that BAR-transduced, long term in vitro-expanded human Tregs retained the xo-expression of Foxp3 and Helios, which are markers for functional human Tregs.

Figure 16:
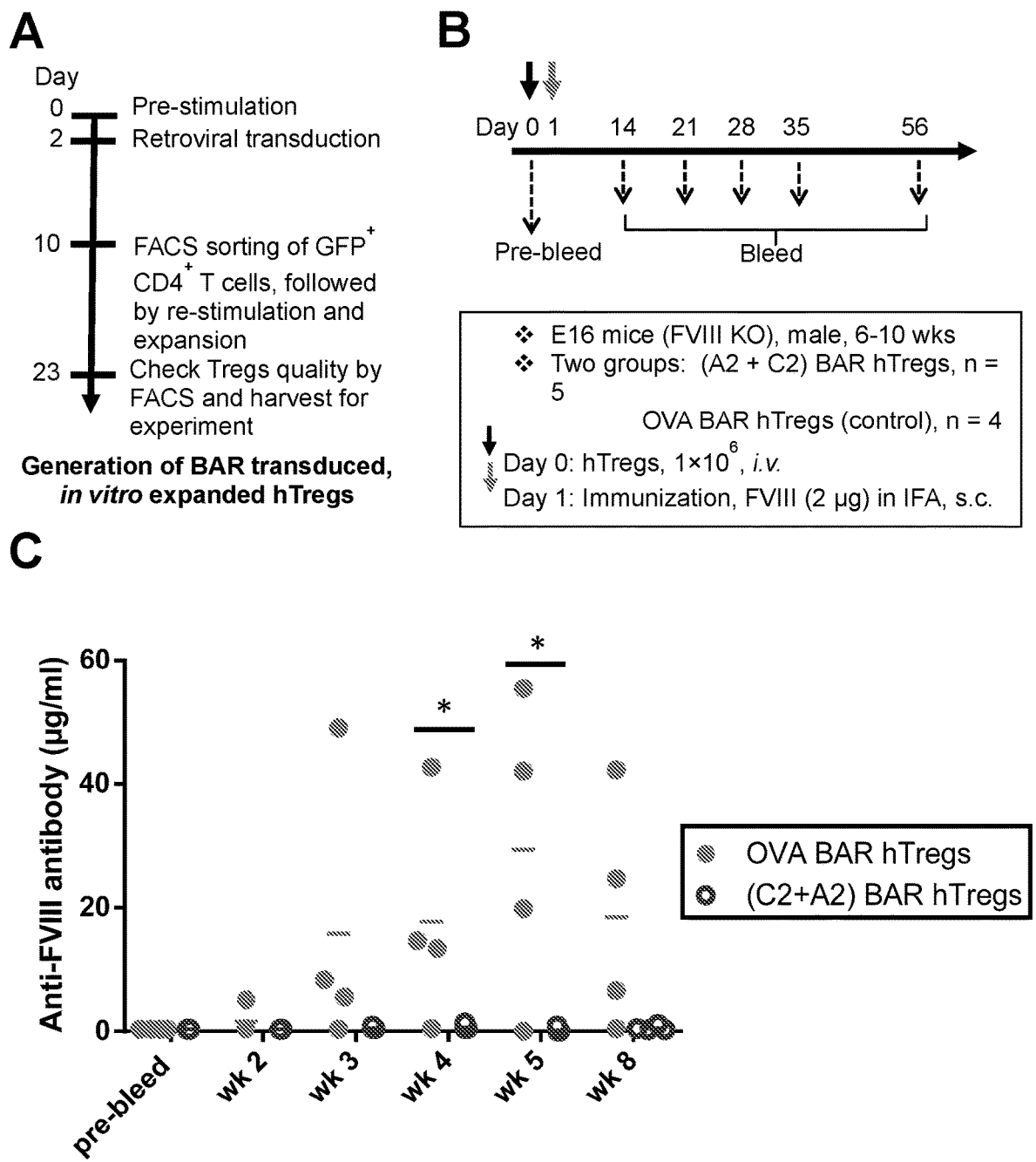

FIG. 16. Suppression of FVIII-specific B cell activity in a xenogeneic mouse model in vivo. FIG. 16A shows a timeline for generation of BAR-transduced and in vitro-expanded human regulatory T cells (Tregs). FIG. 16B outlines the experimental protocol. FIG. 16C shows anti-FVIII antibody levels measured by ELISA assay with a standard curve generated using a mixture of anti-A2 and anti-C2 monoclonal antibodies. (*$p<0.05$, student t test, single tail distribution.) This figure shows that adoptive transfer of the mixture containing equal number of A2 BAR transduced human Tregs and C2 BAR transduced human Tregs ((A2+C2) BAR hTregs) prevented anti-FVIII antibody development in all 5 mice in the group, which confirmed the effectiveness of BAR-Treg therapy for treating unwanted immune responses.

Figure 17:
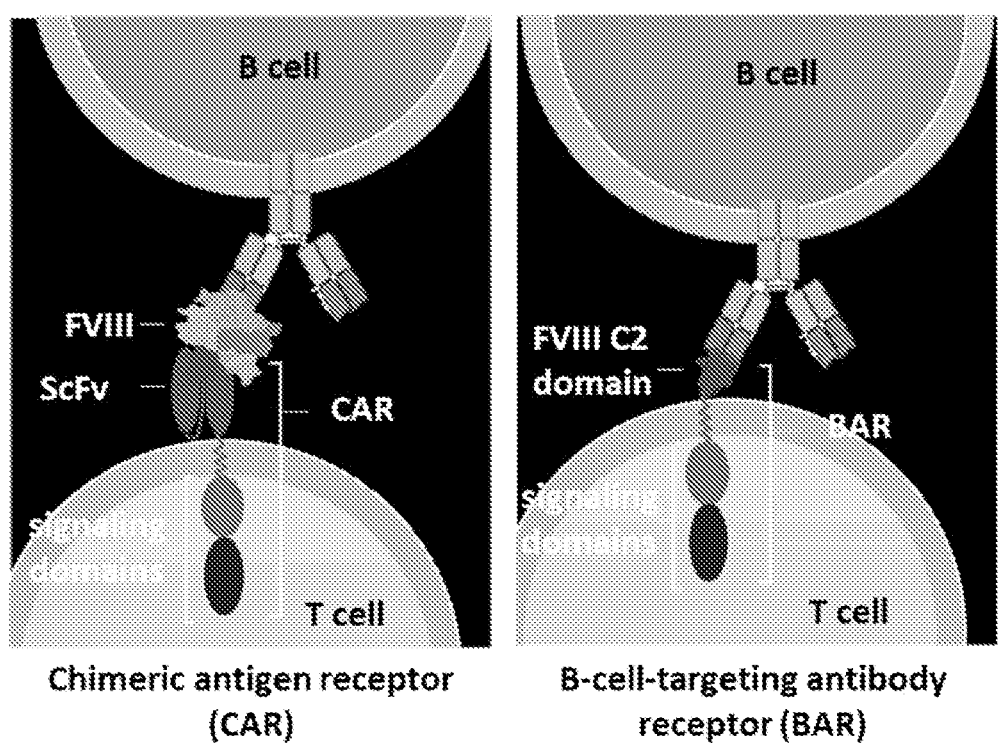

FIG. 17. Schematic diagram of chimeric antigen receptor (CAR) and B-cell-targeting antibody receptor (BAR) constructs. On the left (CAR), a T cell engineered to express a single chain antibody specific for a target antigen (such as FVIII) is bound to target antigen (such as FVIII) which in turn is bound to an FVIII-specific B cell. On the right (BAR), a T cell is engineered to express a target antigen domain (such as FVIII C2) which is recognized by and bound to a FVIII-specific B cell.

Figure 18:
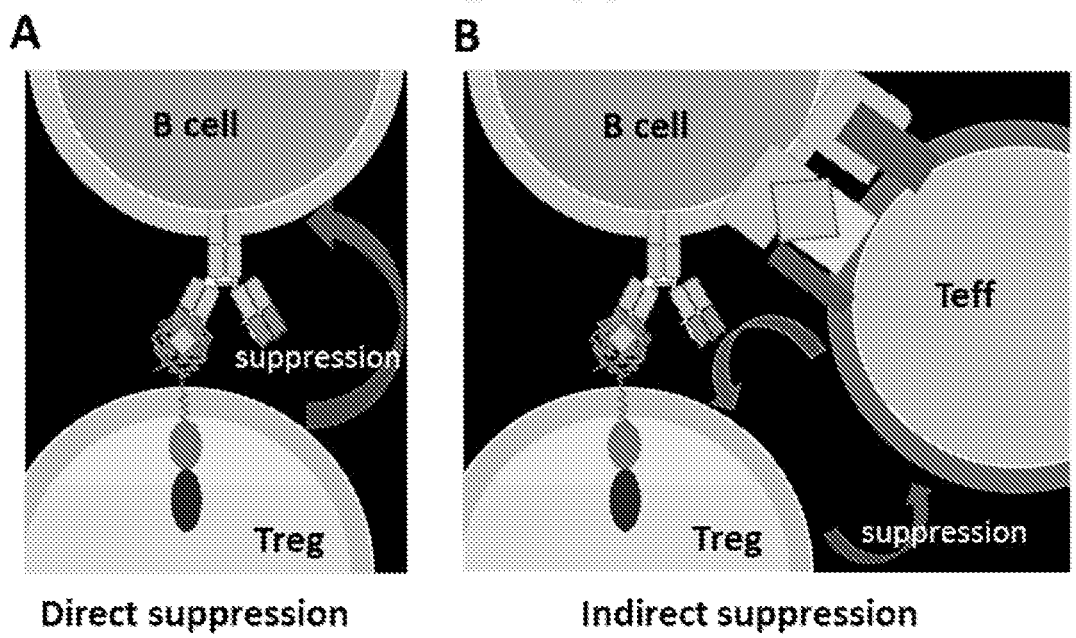

FIG. 18. Proposed mechanism of action for the ability of engineered regulatory T cells as described herein to suppress B cell responses. FIG. 18A shows that regulatory T cells may directly suppress B cells. FIG. 18B shows that engineered regulatory T cells may indirectly suppress B cell via effector T cells.

Figure 19:
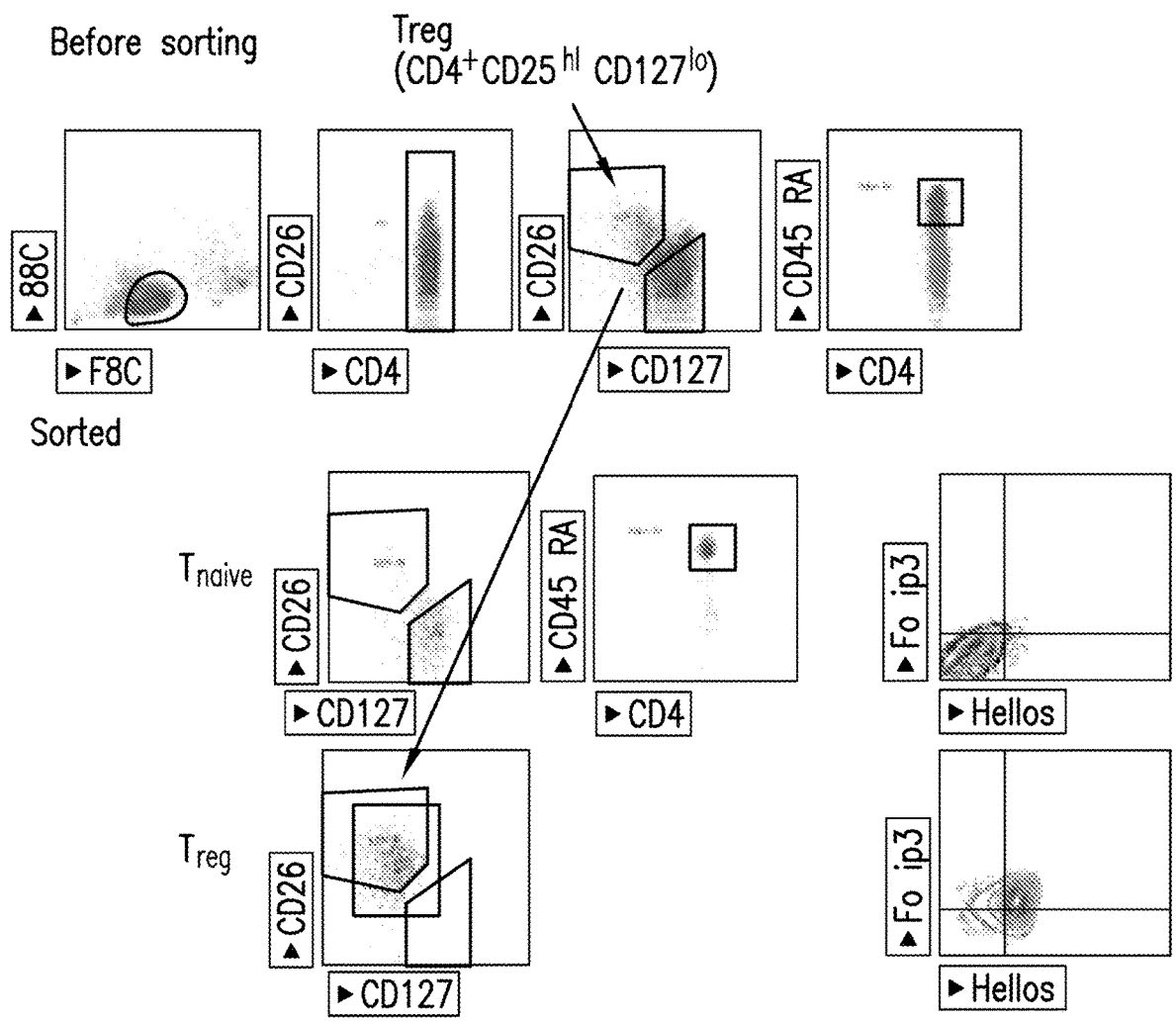

FIG. 19. Comparison of cell populations before FACS sorting and after FACS sorting. As shown, the CD4$^+$CD25$^{hi}$CD127$^{lo}$ regulatory T cells also express Foxp3 and Helios.

Figure 20:
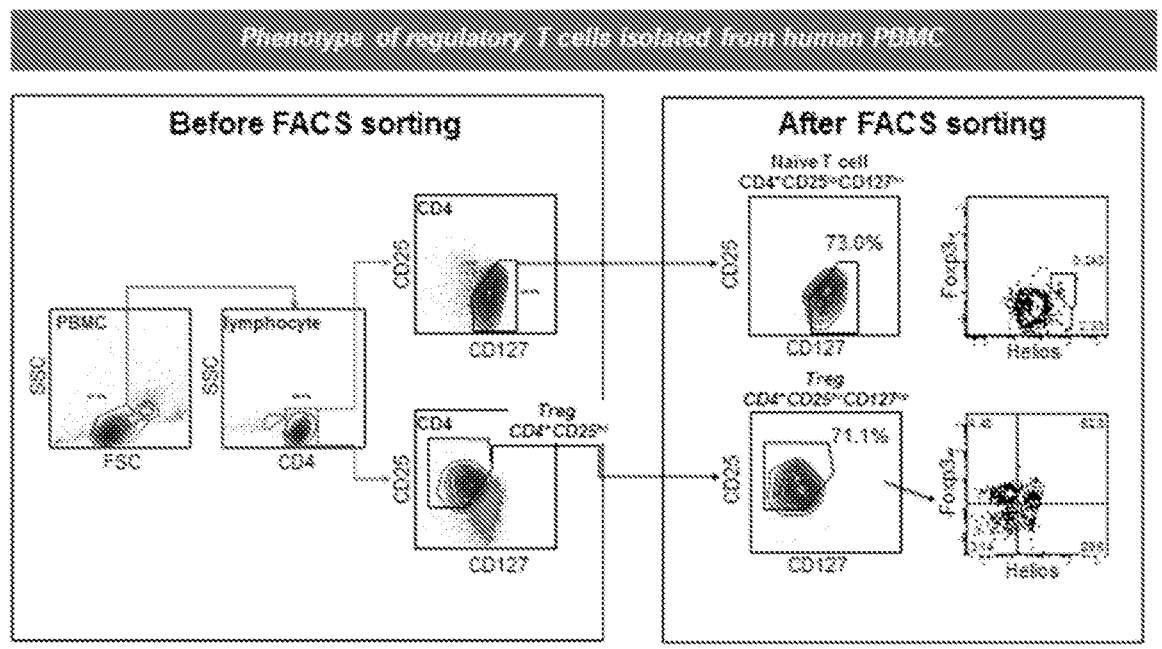

FIG. 20. Illustration of FACS sorting of regulatory T cells to obtain regulatory T cells having a CD4$^+$CD25$^{hi}$CD127$^{lo}$Foxp3$^+$Helios$^+$phenotype. As shown, the CD4$^+$CD25$^{hi}$CD127$^{lo}$cells also express Foxp3 and Helios.

DETAILED DESCRIPTION

Described herein are agents and methods for targeting antigen-specific B cells using engineered regulatory T cells or cytotoxic T cells and bispecific antibodies. The agents include engineered human cytotoxic T cells (such as CD8+ or NK T cells), engineered human regulatory T cells, and bi-specific antibodies. The agents and methods can be used to reduce undesirable immune responses, including minimizing or eliminating adverse, undesirable immune responses, such as may arise in response to protein therapy for genetic diseases, or to allergens or toxins used in immunotoxins. The approaches described herein use the engineered regulatory T cells, or bispecific antibodies to suppress or kill antigen-specific B cells that are the precursors for antibody production against the target antigen (e.g., therapeutic proteins or allografts), thus reducing or eliminating the undesired antibody response.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein "subject" denotes any mammal, including humans.

Cytotoxic T cells and natural killer (NK) T cells play an important role for immune defense against intracellular pathogens, including viruses and bacteria, and for tumor surveillance. Cytotoxic T cells recognize surface markers on other cells in the body and label those cells for destruction. The most well-understood cytotoxic T cells are those that express CD8 (CD8+ T cells), and NK T cells.

Regulatory T cells suppress immune responses of other cells. They come in several forms with the most well-understood being those that express CD4, CD25, Foxp3, and Helios (CD4$^+$CD25$^+$ Tregs). These cells are involved in shutting down immune responses after they have successfully eliminated invading organisms, and in preventing autoimmunity.

Previously, T cells have been rendered specific for cancer antigens (CARs) in order to specifically destroy cancer cells, e.g., in order to promote an immune response. However, the approaches described herein use engineered cytotoxic T cells or engineered regulatory T cells in order to modulate (turn off) undesirable immune responses, e.g., to reduce an immune response. The use of engineered cytotoxic T cells, engineered regulatory T cells, or bispecific antibodies described herein to specifically target antigen-specific B cells for killing has not heretofore been described.

In accordance with some embodiments, a regulatory T cell or cytotoxic T cell is engineered to express on its cell surface a target antigen or a domain thereof recognized by an antigen-specific B cell. Such engineered regulatory T cells or cytotoxic T cells can be used in methods of targeting antigen-specific B cells, comprising exposing B cells specific to a target antigen to regulatory T cells or cytotoxic T cells that express on their cell surface the target antigen or a domain thereof recognized by the antigen-specific B cells. In accordance with such methods, the engineered regulatory T cells or engineered cytotoxic T cells are brought into proximity/contact with the antigen-specific B cells via the target antigen or domain thereof expressed on the surface of the T cells and bound by the antigen-specific B cells, such that the engineered T cells induce killing of the antigen-specific B cells.

In accordance with other embodiments, a regulatory T cell or cytotoxic T cell is engineered to express on its cell surface a single chain antibody that is specific for a target antigen. Such engineered regulatory T cells or cytotoxic T cells can be used in methods of targeting antigen-specific B cells, comprising exposing B cells specific to a target antigen to (i) regulatory T cells or cytotoxic T cells that express on their cell surface a single chain antibody specific for the target antigen and (ii) the target antigen (or a fragment thereof that can be bound by both the single chain antibody and antigen-specific B cells). In some embodiments, the single chain antibody is bound to the target antigen or domain thereof recognized by the antigen specific B cells before exposure to the antigen specific B cells.

In accordance with other embodiments, a bispecific antibody is prepared that has a T cell-binding end and a B cell-targeting end, wherein the B cell-targeting end comprises a domain of the target antigen recognized by the antigen-specific B cells cloned into one IgG arm, and a T cell-binding moiety cloned into the other arm. In some embodiments, the T cell-binding end comprises an anti-CD8 single chain antibody or an anti-CD3e single chain antibody. In other embodiments, the T cell-binding end comprises an antibody that specifically recognizes the regulatory T cell. The bispecific antibodies are useful in methods comprising exposing antigen-specific B cells to regulatory T cells or cytotoxic T cells bound by the bispecific antibodies. In such methods, the regulatory T cells or cytotoxic T cells are brought into proximity/contact with the antigen-specific B cells via binding between the bispecific antibody and the T cells and antigen-specific B cells, such that the regulatory T cells or cytotoxic T cells induce suppression or killing of the antigen-specific B cells.

Cytotoxic T cells useful herein may be selected from CD8+ T cells and natural killer (NK) T cells. In accordance with any of these embodiments, the cytotoxic T cell may maintain its phenotype after transduction and long-term expansion.

Regulatory T cells useful herein may be isolated by Fluorescent Activated Cell Sorting (FACS) based on the cell surface markers, such as CD4, CD 25, and CD127. In some embodiments, regulatory T cells of interest include those with little or no expression of CD127 (CD127$^{lo}$), and/or with high expression of CD25 (CD25$^{hi}$). In some embodiments, the regulatory T cells express CD4, CD25, Foxp3, and Helios. In some embodiments, the regulatory T cells are CD4$^+$CD25$^{hi}$CD127$^{lo}$Foxp3$^+$Helios$^+$ regulatory T cells (FIG. 8, FIG. 9). In other embodiments, the regulatory T cells are CD4$^+$CD25$^{hi}$CD127$^{lo}$Foxp3$^+$ regulatory T cells, CD4$^+$CD25$^{hi}$Foxp3$^+$ regulatory T cells or CD4$^+$CD25$^{hi}$Foxp3$^+$Helios$^+$ regulatory T cells. In accordance with any of these embodiments, the regulatory T cell may maintain its phenotype after transduction and long-term expansion.

In accordance with any of these embodiments, autologous polyclonal regulatory T cells and HLA-matched allogeneic regulatory T cells can be used as donor cells. In some embodiments, endogenous TCR on donor regulatory T cells can be inactivated using existing technologies such as CRISPR/Cas9.

In accordance with any of these embodiments, autologous polyclonal cytotoxic T cells and HLA-matched allogeneic cytotoxic T cells can be used as donor cells. In some embodiments, endogenous TCR on donor cytotoxic T cells can be inactivated using existing technologies such as CRISPR/Cas9.

Engineered regulatory T cells or cytotoxic T cells as described herein can be made by adapting methods known in the art, including the methods of isolating and transducing T cells described in U.S. Provisional Application 61/821,857 and U.S. patent application Ser. No. 14/889,962, filed Nov. 9, 2015 (published as US 2016/0194605), which are incorporated herein by reference in their entireties. Gene and protein sequences of target antigens and domains thereof recognized by antigen-specific B cells are known in the art, and include those set forth in U.S. Provisional Application 61/821,857 and U.S. application Ser. No. 14/889,962 and in U.S. Provisional Application 61/990,456 and PCT Application PCT/US15/29642, filed May 7, 2015 (published as WO 2015/171863), which are incorporated herein by reference in their entireties.

In accordance with any of these embodiments, the cytotoxic T cells or regulatory T cells may be transduced with a B-cell-targeting antibody receptor (BAR) construct comprising (i) an extracellular domain comprising the target antigen or a domain thereof recognized by the B cell and (ii) an intracellular signaling domain. For cytotoxic T cells, the intracellular signaling domain may comprise one or more signaling domains, such as one or more signaling domains of CD28-CD3ζ, 4-1BB, and ICOS. For regulatory T cells, the intracellular signaling domain may comprise one or more signaling domains, such as one or more signaling domains of CD28-CD3ζ, 4-1BB, ICOS, and CTLA-4.

In accordance with any of these embodiments, the target antigen or domain thereof recognized by the antigen-specific B cells may be a therapeutic agent, such as a therapeutic protein or an allergen or toxins used as an immunotoxin, such as a therapeutic protein selected from human clotting factor VIII, human clotting factor IX, the C2 domain of human clotting factor VIII, the A2 domain of human clotting factor VIII, and the A2-C2 domain of human clotting factor VIII, an antigen associated with diabetes, such as insulin or glutamic acid decarboxylase (GAD65), an antigen associated with uveitis, such as arrestin, myelin basic protein (MBP) or other antigens associated with multiple sclerosis, such as thyroperoxidase (TPO), an antigen associated with thyroiditis, such as thyroperoxidase (TPO), an antigen associated with myasthenia gravis, such as acetylcholine receptor (AchR), an antigen associated with antiphospholipid syndrome (APS) (as may be associated with systemic lupus erythematosus ("SLE" or "Lupus") or repeated miscarriage), or a domain of any of the foregoing recognized by the B cell. Alternatively, the target antigen may be associated with a transplant, such as a cell, tissue, or organ of an allograft transplant. Alternatively, the target antigen may be an antigen associated with an allergy, allergic response, or asthma.

Any of the engineered T cells or antibodies described herein can be used in any of the methods outlined above. In some embodiments, the method is effected in a patient suffering from or at risk of developing an undesirable immune response to the target antigen. In some embodiments, the patient is suffering from autoimmune diseases, anti-drug antibody development, or allergy. In some embodiments, the patient is suffering from an autoimmune disorder, such as one or more selected from the group consisting of multiple sclerosis, diabetes, uveitis, thyroiditis, myasthenia gravis, or antiphospholipid syndrome (APS), or is receiving a biotherapeutic treatment for a genetic disease, such as Pompe's or hemophilia (including hemophilia A and hemophilia B). In specific embodiments, the patient is a hemophilia patient (including hemophilia A and hemophilia B). In other specific embodiments, the patient is receiving a transplant. In other specific embodiments, the patient is suffering from or at risk of developing an undesired immune response to Factor VIII therapy. In accordance with any of these embodiments, the method may be effective to reduce or prevent the patient's immune response to the target antigen. In other specific embodiments, the patient suffers from an allergy or allergic response or asthma, and target antigen may be an antigen associated with the allergy or allergic response or asthmatic response, and the method may be effective to reduce or eliminate the allergy or allergic response or to treat the asthma or reduce the asthmatic response.

In accordance with any of the regulatory T cell embodiments, the target antigen is not desmoglein (Dsg) 3 or a domain thereof recognized by antigen-specific B cells. In some embodiments, the target antigen is not Dsg3 EC1, EC2, EC3, or EC4. In accordance with any of the cytotoxic T cell embodiments, the target antigen is not desmoglein (Dsg) 3 or a domain thereof recognized by antigen-specific B cells. In some embodiments, the target antigen is not Dsg3 EC1, EC2, EC3, or EC4.

EXAMPLES

T cell isolation, activation, transduction, flow-cytometry, cell proliferation assays, JAM assays, and ELISPOT assays were conducted according to procedures known in the art, and can be conducted in manners similar to those described in U.S. Provisional Application 61/821,857, U.S. Provisional Application 61/990,456, U.S. application Ser. No. 14/889,962, filed Nov. 9, 2015 (published as US 2016/0194605), and PCT Application PCT/US15/29642, filed May 7, 2015 (published as WO2015/171863), which are incorporated herein by reference in their entireties.

Example 1—Construction of FVIII-C2 B Cell Antibody Receptor (BAR) Construct

A mouse CD4 N-terminal signaling peptide, FVIII-C2, human CD28 transmembrane, intracellular, human CD3, an internal ribosomal entry site (IRES) and GFP gene were cloned into a vector to create the FVIII-C2 BAR construct. A control construct where the gene encoding OVA replaced FVIII-C2 also was prepared (the OVA-BAR construct). The IRES allows the BAR construct and GFP to be expressed as a single mRNA molecule, such that measurement of GFP correlates to BAR construct expression. The results in FIG. 3 show that the genes were successfully cloned into the vector.

This BAR construct can be used to transduce cytotoxic T cells or regulatory T cells.

Example 2—Expression of BAR on the Surface of Cytotoxic T Cells

Figure 4:
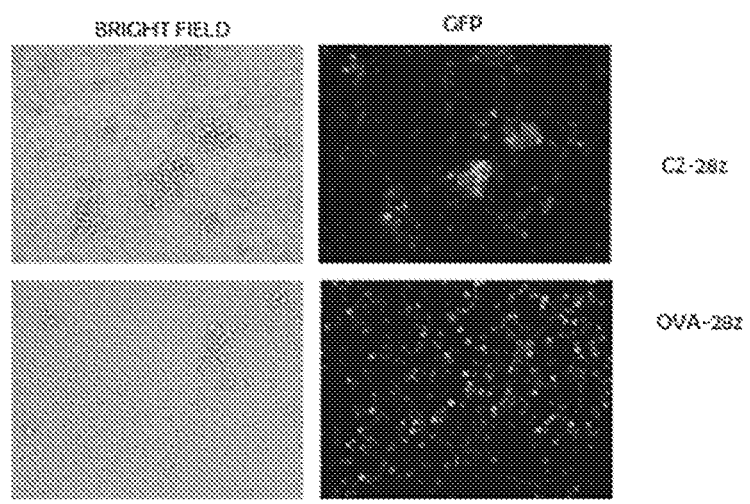

Isolated CD8+ cytotoxic T cells were activated and transduced with replication deficient BAR retrovirus using retronectin. GFP expression was analyzed 24 hrs post transduction. FIG. 4 shows that GFP expression can be visualized in both FVIII-C2 BAR and OVA transduced T cells, which shows that both constructs were efficiently transduced into T cells.

Flow cytometry using known antibodies against FVIII-C2 and OVA was used to determine whether the BAR construct was expressed on the T cell surface. Anti-A2 and anti-OVA antibodies were used as controls. The results in FIG. 5 show that the C2-BAR construct was expressed on the T cell surface.

To observe the proliferation competency of the BAR-expressing T cells, T cells were transduced and rested for 10 days, and then irradiated-PBMC pulsed with anti-FVIII sera were added at 2:1 to BAR-expressing T cells. Cells were grown for 48 hrs and radioactive tritiated thymidine uptake assay was performed for 24 hrs. The thymidine uptake by the proliferating T cells was measured. The results in FIG. 6 show an increase in proliferation of C2-BAR T cells proliferation when anti-FVIII sera was used, as compared to the controls.

Example 3—Killing of B Cells by BAR-Transduced Cytotoxic T Cells

To determine whether FVIII-C2 BAR transduced cytotoxic T cells are able to kill α-FVIII hybridoma, a JAM test was conducted with 2C11 (anti-C2) B cell hybridoma cells. The 2C11 (anti-C2) B cell hybridoma cells were radiolabeled with tritiated thymidine for 24 hrs and C2-BAR transduced CD8+ T cells were added at various ratios and incubated for 5 hrs. At the end of the test, radioactivity was measured. As shown in FIG. 7, a decrease in radiolabeled hybridoma cells, which corresponds to reduced viability of B cell hybridoma cells, was detected compare to the control (OVA transduced T cell). The results show that FVIII-C2 BAR transduced T cells are able to kill B cell hybridoma cells.

To quantify the hybridoma cell viability, an ELISPOT assay was carried out with FVIII-C2 BAR transduced CD8+ T cells. 2C11 (anti-C2) B cell hybridoma cells were incubated with C2-BAR CD8 T cells at various ratios for 5 hrs and are then grown for 12 hrs on a FVIII coated plate. Number of spots formed at the end of the assay was quantified. The results in FIGS. 8-10 show a decrease in number of spots formed per well (which correlates to the number of viable antibody secreting B cells) in C2-BAR transduced CD8+ T cells compared to that of OVA control.

To observe A2-BAR mediated cytolysis of α-FVIII hybridoma, FVIII A2-BAR transduced CD8 T cells were incubated with α-FVIII hybridoma. Images were taken at 5, 20, 30, 40 and 55 minutes after the incubation. As shown in FIG. 11, cytolysis of the hybridoma by FVIII A2-BAR transduced CD8 T cells was observed.

Example 4—Construction, Expression of BAR on Human CD4+ Regulatory T Cells

Constructs as depicted in FIG. 13A and FIG. 13B were prepared. In particular, constructs comprising a signaling peptide, FVIII-C2 or FVIII-A2, human CD28-CD3 transmembrane/intracellular domains were prepared. As control, a OVA-BAR construct was prepared as illustrated in the figure. A retroviral vector, pRetro-IRES-Zsgreen was used to express the BAR constructs. The GFP reporter gene under the control of the IRES element enables tracking of successfully transduced cells. To confirm the proper expression of BAR, human CD4+ regulatory T cells were retrovirally transduced with either C2 BAR or OVA BAR. Flow cytometry using known antibodies against FVIII-C2 and OVA was used to determine whether the BAR construct was expressed on the T cell surface. The results in FIG. 13C show that the C2-BAR and OVA-BAR constructs were successfully expressed on the transduced regulatory T cells.

This construct also can be also be used to transduce cytotoxic T cells.

Example 5—Functionality of BAR on Transduced Human CD4+ Regulatory T Cells

To determine whether successfully expressed BAR constructs on the transduced regulatory T cells can actually transmit signal and activate the cells upon interaction with cognate B cell or antibody, proliferation response of OVA-BAR transduced human CD4+ T cells was tested. Human CD4+ regulatory T cells were transduced with an OVA-BAR construct in a concentrated retroviral supernatant, labeled with cell proliferation dye eFlour450, and cultured with either cognate anti-OVA antibody or control IgG for 3 days in the presence of irradiated PBMC. Cell proliferation was analyzed by flow cytometry. The cells were gated on live GFP+ cells. The results reported in FIG. 14 show that OVA-BAR-transduced regulatory T cells proliferated specific to anti-OVA IgG but not to control IgG, which confirms that the BAR expressed on the regulatory T cells is functional.

Example 6—Long-Term Maintenance of Phenotype of Transduced Human Regulatory T Cells In order to obtain enough regulatory T cells for adoptive therapy, BAR-transduced regulatory T cells need to be expanded in vitro. One known limitation facing human regulatory T cell therapy is that in vitro expanded human regulatory T cells often quickly lose Foxp3 and/or Helios expression, and suppressive function. To confirm that BAR-transduced, long term in vitro-expanded human regulatory T cells retain the co-expression of Foxp3 and Helios, FACS analysis for Foxp3 and Helios expression was conducted on BAR-transduced regulatory T cells after about 3 weeks in vitro expansion. The results reported in FIG. 15 show that BAR-transduced human regulatory T cells as described herein retain the co-expression of Foxp3 and Helios after long term expansion.

Example 7—Generation of BAR-Transduced, In Vitro-Expanded Human Regulatory T Cells To transduce regulatory T cells with a BAR construct, human regulatory T cells were first stimulated for two days.

Stimulated cells were transduced with concentrated retroviral supernatant. The transduced cells were maintained and rested for 8 days without additional stimuli. The GFP+ CD4 cells were isolated by FACS sorting, and used for re-stimulation and expansion. The quality of the transduced regulatory T cells was checked by FACS, and the cells were harvest for experiment. A timeline for generation of BAR-transduced regulatory T cells is shown in FIG. 16A.

Example 8—In Vivo Suppression of Anti-FVIII Antibody Development by BAR Regulatory T Cell Therapy in Naïve E16 Mice A xenogeneic mouse model was used to validate the effectiveness of BAR-transduced regulatory T cell therapy. As outlined in FIG. 16B, male 6-10-week old E16 FVIII KO mice were divided into two groups. On day one, five mice were intravenously injected with $1 \times 10^6$ cells containing equal number of C2-BAR-transduced human Tregs and A2-BAR-transduced human regulatory T cells. As control, four mice received same number of OVA-BAR-transduced human regulatory T cells. Both groups were actively immunized with FVIII in IFA adjuvant on day 1. The anti-FVIII antibody level was monitored by ELISA assay with a standard curve generated using a mixture of anti-A2 and anti-C2 monoclonal antibodies. The results reported in FIG. 16C show that the group of mice treated with (C2+A2) BAR-transduced regulatory T cells had lower amounts of anti-FVIII antibody compared to the control group. Thus, (C2+A2) BAR-transduced regulatory T cells essentially prevented anti-FVIII antibody development, confirming the effectiveness of BAR-transduced regulatory T cell therapy in controlling unwanted immune response.

What is claimed is:

1. A human regulatory T cell that expresses on its cell surface a target antigen or a domain thereof recognized by an antigen-specific B cell, wherein the target antigen or domain thereof is human clotting factor VIII, C2 domain of human clotting factor VIII, A-2 domain of human clotting factor VIII, or A2-C2 domain of human clotting factor VIII, wherein the regulatory T cell is transduced with a B-cell-targeting antibody receptor (BAR) construct comprising (i) an extracellular domain comprising the target antigen or domain thereof and (ii) an intracellular signaling domain comprising one or more signaling domains of CD28-CD3ζ, 4-1BB, ICOS, and CTLA-4.

2. The regulatory T cell of claim 1, wherein the target antigen is associated with hemophilia.

3. A human cytotoxic T cell or natural killer T cell that expresses on its cell surface a target antigen or a domain thereof recognized by an antigen-specific B cell, wherein the target antigen or domain thereof is human clotting factor VIII, C2 domain of human clotting factor VIII, A-2 domain of human clotting factor VIII, or A2-C2 domain of human clotting factor VIII, wherein the T cell is transduced with a B-cell-targeting antibody receptor (BAR) construct comprising (i) an extracellular domain comprising the target antigen or domain thereof and (ii) an intracellular signaling domain comprising human CD28 and/or human CD3ζ.

4. The cytotoxic T cell or natural killer T cell of claim 3, wherein the intracellular signaling domain comprises CD28-CD3ζ.

5. The cytotoxic T cell or natural killer T cell of claim 3, wherein the cytotoxic T cell is a CD8+T cell.

6. The cytotoxic T cell or natural killer T cell of claim 3, wherein said target antigen is associated with hemophilia.

7. The regulatory T cell of claim 1 that expresses CD4, CD25, Foxp3, or Helios.

8. The cytotoxic T cell or natural killer T cell of claim 3, wherein the intracellular signaling domain comprises CD3ζ.

9. A B-cell-targeting antibody receptor (BAR) construct comprising (i) an extracellular domain comprising a target antigen or domain thereof and (ii) an intracellular signaling domain, wherein the target antigen or domain thereof is human clotting factor VIII, C2 domain of human clotting factor VIII, A-2 domain of human clotting factor VIII, or A2-C2 domain of human clotting factor VIII and the intracellular signaling domain comprises one or more signaling domains of CD28-CD3ζ, 4-1BB, ICOS, and CTLA-4.

10. The construct of claim 9, wherein the intracellular signaling domain comprises CD28-CD3ζ.

11. The construct of claim 9, wherein said target antigen is associated with hemophilia.

12. A B-cell-targeting antibody receptor (BAR) construct comprising (i) an extracellular domain comprising a target antigen or domain thereof and (ii) an intracellular signaling domain, wherein the target antigen or domain thereof is human clotting factor VIII, C2 domain of human clotting factor VIII, A-2 domain of human clotting factor VIII, or A2-C2 domain of human clotting factor VIII and the intracellular signaling domain comprises human CD28 and/or CD3ζ.

13. The construct of claim 9, wherein said target antigen is associated with hemophilia.

14. A human cytotoxic T cell or natural killer T cell that expresses on its cell surface a target antigen or a domain thereof recognized by an antigen-specific B cell, wherein the target antigen or domain thereof is human clotting factor VIII, C2 domain of human clotting factor VIII, A-2 domain of human clotting factor VIII, or A2-C2 domain of human clotting factor VIII, wherein the T cell is transduced with a B-cell-targeting antibody receptor (BAR) construct comprising (i) an extracellular domain comprising the target antigen or domain thereof and (ii) an intracellular signaling domain comprising one or more signaling domains of CD28-CD3ζ, 4-1BB, ICOS, and CTLA-4.

15. The cytotoxic T cell or natural killer T cell of claim 14, wherein the cytotoxic T cell is a CD8+T cell.

16. The cytotoxic T cell or natural killer T cell of claim 14, wherein said target antigen is associated with hemophilia.

* * * * *